United States Patent
Saiki et al.

(10) Patent No.: US 10,208,692 B2
(45) Date of Patent: Feb. 19, 2019

(54) MISFIRE DETECTING SYSTEM FOR ENGINE

(71) Applicant: Mazda Motor Corporation, Aki-gun, Hiroshima (JP)

(72) Inventors: Akio Saiki, Hiroshima (JP); Kenichi Ogasawara, Hiroshima (JP)

(73) Assignee: Mazda Motor Corporation, Aki-gun, Hiroshima (JP)

( * ) Notice: Subject to any disclaimer, the term of this patent is extended or adjusted under 35 U.S.C. 154(b) by 4 days.

(21) Appl. No.: 15/464,026

(22) Filed: Mar. 20, 2017

(65) Prior Publication Data

US 2017/0276083 A1 Sep. 28, 2017

(30) Foreign Application Priority Data

Mar. 23, 2016 (JP) ................ 2016-058513

(51) Int. Cl.
*F02D 41/22* (2006.01)
*F02D 41/26* (2006.01)
*G01M 15/05* (2006.01)
*G01M 15/11* (2006.01)
*G01N 9/00* (2006.01)
*G01P 15/00* (2006.01)
*F02D 41/02* (2006.01)
*F02D 41/14* (2006.01)

(52) U.S. Cl.
CPC ............. *F02D 41/22* (2013.01); *F02D 41/26* (2013.01); *G01M 15/05* (2013.01); *G01M 15/11* (2013.01); *F02D 41/021* (2013.01); *F02D 41/1498* (2013.01); *F02D 2041/228* (2013.01); *F02D 2200/0414* (2013.01); *F02D 2200/1015* (2013.01); *F02D 2200/501* (2013.01); *G01N 9/00* (2013.01); *G01P 15/00* (2013.01)

(58) Field of Classification Search
CPC ....................................... F02D 41/22
See application file for complete search history.

(56) References Cited

U.S. PATENT DOCUMENTS

| | | | | |
|---|---|---|---|---|
| 5,278,760 A | * | 1/1994 | Ribbens | F02D 41/1498 123/436 |
| 5,606,120 A | * | 2/1997 | Daicho | G01M 15/11 123/406.27 |
| 6,935,313 B2 | * | 8/2005 | Jacobson | F02D 35/023 123/406.22 |

(Continued)

FOREIGN PATENT DOCUMENTS

| | | |
|---|---|---|
| JP | 2006183502 A | 7/2006 |
| JP | 2007192081 A | 8/2007 |

(Continued)

*Primary Examiner* — Hussein Elchanti
*Assistant Examiner* — Michael A Berns
(74) *Attorney, Agent, or Firm* — Alleman Hall Creasman & Tuttle LLP

(57) ABSTRACT

A misfire detecting system for an engine of a vehicle that detects a misfire of the engine is provided, which includes a processor. The processor determines whether a misfire has occurred by examining whether a fluctuation of a crank angle of the engine is equal to or greater than a determination reference value, acquires a value relating to a density of intake air introduced into the engine, and adjusts the determination reference value according to the value related to the density.

9 Claims, 7 Drawing Sheets

(56) References Cited

U.S. PATENT DOCUMENTS

| | | | | |
|---|---|---|---|---|
| 7,210,456 | B2* | 5/2007 | Moriya | F02D 41/1497 |
| | | | | 123/435 |
| 9,068,522 | B2* | 6/2015 | McConville | F02D 41/1454 |
| 9,243,978 | B2* | 1/2016 | Wada | G01M 15/11 |
| 9,453,783 | B2* | 9/2016 | Yu | G01M 15/11 |
| 9,951,710 | B2* | 4/2018 | Sugimoto | F02D 41/3094 |
| 2016/0222893 | A1* | 8/2016 | Ohta | F02P 9/002 |
| 2017/0276084 | A1* | 9/2017 | Saiki | F02D 41/0007 |

FOREIGN PATENT DOCUMENTS

| | | | |
|---|---|---|---|
| JP | 2011085081 | A | 4/2011 |
| JP | 2014136989 | A | 7/2014 |

* cited by examiner

MISFIRE DETECTING SYSTEM FOR ENGINE

BACKGROUND

The present invention relates to a misfire detecting system for an engine, which determines an occurrence of misfire.

Conventionally, vehicles provided with engines generally perform a misfire determination in which a misfire of an engine is detected. For example, JP2014-136989A discloses an art for calculating a rotational fluctuation of an engine by using a crank angle sensor and performing the misfire determination based on the rotational fluctuation. Specifically in such an art, it is determined that the misfire (one of a single misfire, continuous misfires, and intermittent misfires) has occurred if the rotational fluctuation of the engine exceeds a given misfire determination reference value.

Incidentally, an intake air introducing amount (charging amount) into each cylinder tends to slightly vary depending on the shape of an intake manifold, the smoothness of an intake air flow into the cylinder (or, roughness of the intake air flow), etc. Especially in a situation where a density of intake air (intake air density) introduced into the cylinders becomes high, such a variation of the intake air introducing amount among the cylinders becomes large. As a result, the combustion variation among the cylinders may become large and the crank angle may fluctuate greatly. With the art for determining the occurrence of a misfire based on the crank angle as JP2014-136989A described above, there is a possibility that the crank angle fluctuation is falsely determined as a misfire.

SUMMARY

The present invention is made in view of solving the issues of the conventional arts described above, and aims to provide a misfire detecting system for an engine, which performs a misfire determination based on a fluctuation of a crank angle of the engine at a high accuracy by taking into consideration a density of intake air introduced into the engine.

According to one aspect of the present invention, a misfire detecting system for an engine of a vehicle that detects a misfire of the engine is provided, which includes a processor. The processor determines whether the misfire has occurred by examining whether a fluctuation of a crank angle of the engine is equal to or greater than a determination reference value, acquires a value related to a density of intake air introduced into the engine, and adjusts the determination reference value according to the value related to the density.

According to this configuration, the misfire determination reference value used to determine the fluctuation of the crank angle is set by taking into consideration the intake air density, and the misfire determination is performed by using this misfire determination reference value. Therefore, it is possible to prevent the crank angle fluctuation, which is caused by a variation of intake air introducing amounts among cylinders of the engine becoming large due to a high intake air density, from being falsely determined to have been caused by a misfire of the engine. Thus, the false determination of the misfire when the intake air density is high is suitably prevented while securing an accuracy of the misfire determination when the intake air density is low. As a result, the accuracy of the misfire determination is improved.

The processor may change the determination reference value based on an engine speed and an engine load, and a change amount of the determination reference value in accordance with the value related to the density is larger when the engine speed is high, compared to when the engine speed is low.

According to this configuration, a suitable determination reference value is set according to the engine speed and load. Further, within a high engine speed range, the determination reference value is set to reflect the influence of the intake air density more than within a low engine speed range. Thus, the determination reference value is set suitably by taking into consideration a characteristic that the crank angle fluctuation becomes large within the high engine speed range under a low temperature. Therefore, the false determination of the misfire is effectively prevented.

The processor may adjust the determination reference value to a first value when the value related to the density exceeds a given range, adjust the determination reference value to a second value when the value related to the density falls below the given range, and adjust the determination reference value between the first and second values according to the value related to the density when the value related to the density is within the given range.

According to this configuration, when the value related to the density is between the range where the determination reference value is set to the first value and the range where the determination reference value is set to the second value (the given range), the misfire determination reference value is suitably changed between the first and second values according to the value related to the density by taking into consideration a responsiveness of a sensor used to acquire the value related to the density, etc.

The processor may acquire a temperature of one of intake air introduced into the engine and outdoor air, as the value related to the density.

According to this configuration, the determination reference value is set based on one of the intake air temperature and the outdoor air temperature, which appropriately indicates the intake air density.

The engine may be provided with a turbocharger. The processor may acquire a temperature of intake air introduced into the engine as the value related to the density.

According to this configuration, since the temperature of the intake air turbocharged by the turbocharger is used as the value related to the density, the determination reference value is set based on an index which appropriately indicates the intake air density producing the variation of the intake air introducing amounts among the cylinders.

The processor may obtain an angular acceleration of the crank angle of the engine and determine that the misfire of the engine has occurred when a fluctuation rate of the angular acceleration is equal to or greater than the determination reference value. The processor may adjust the determination reference value to be higher when the intake air density corresponding to the value related to the density is high, compared to when the intake air density is low.

According to this configuration, the misfire determination is performed based on the fluctuation rate (absolute value) of the crank angular acceleration. Therefore, compared to a case of performing the misfire determination based on a fluctuation of a crank angular speed or a magnitude of the crank angular acceleration, the fluctuation of the crank angle caused by the misfire is suitably captured, which improves the accuracy of the misfire determination.

When the misfire of the engine is determined to have occurred, the processor may turn on an alarm lamp for informing of an abnormality relating to the misfire of the engine.

According to this configuration, a driver is suitably informed of an abnormality relating to the misfire of the engine.

DETAILED DESCRIPTION OF EMBODIMENT

Hereinafter, a misfire detecting system for an engine according to one embodiment of the present invention is described with reference to the appended drawings.

<System Configuration>

Figure 1:
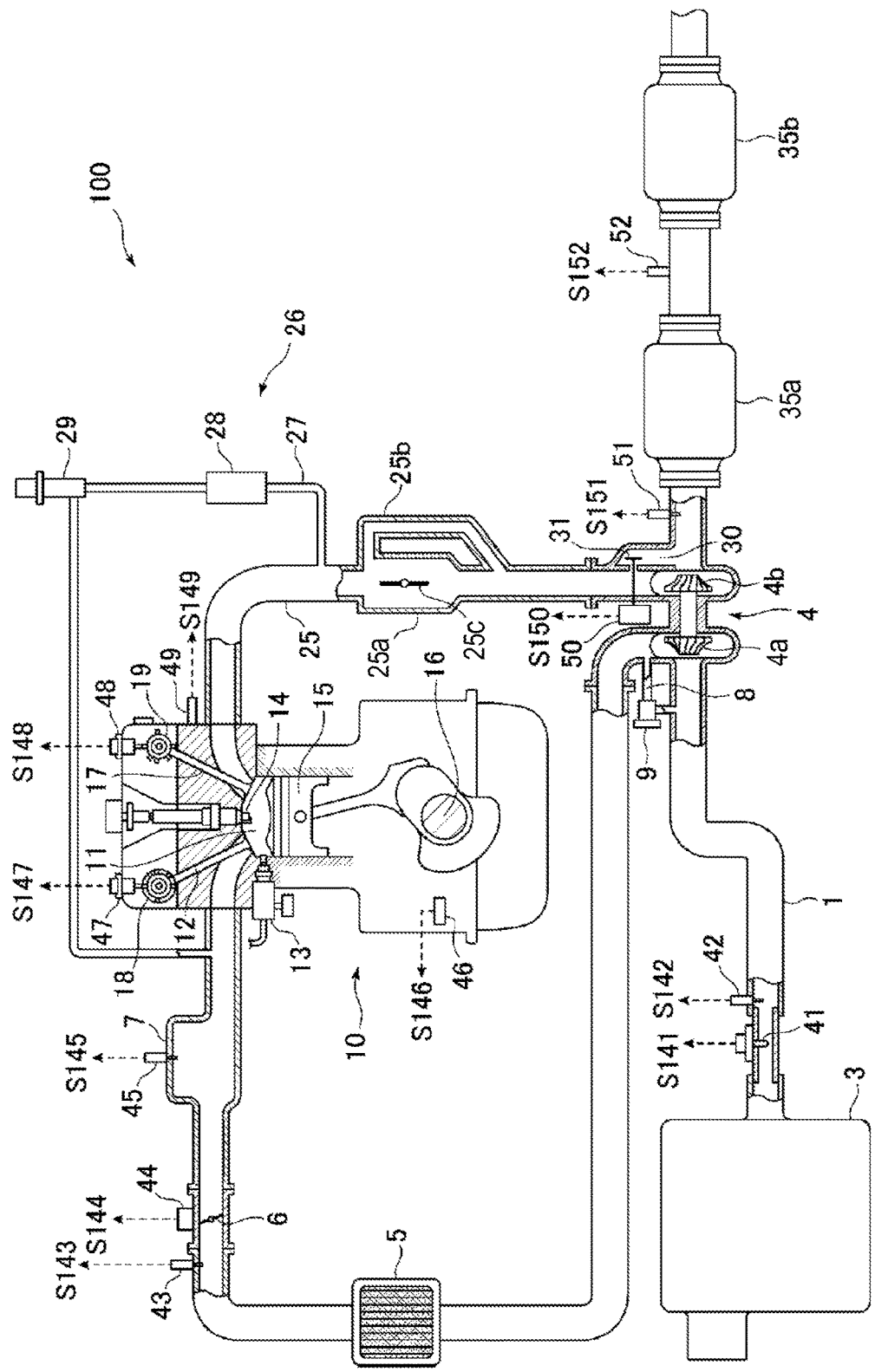
FIG. 1 is a schematic view of an engine system to which a misfire detecting system for an engine according to one embodiment of the present invention is applied.

First, an engine system to which the misfire detecting system for the engine according to this embodiment of the present invention is applied is described with reference to FIGS. 1 and 2. FIG. 1 is a schematic view of the engine system, and FIG. 2 is a block diagram illustrating an electric configuration of the misfire detecting system.

Figure 2:
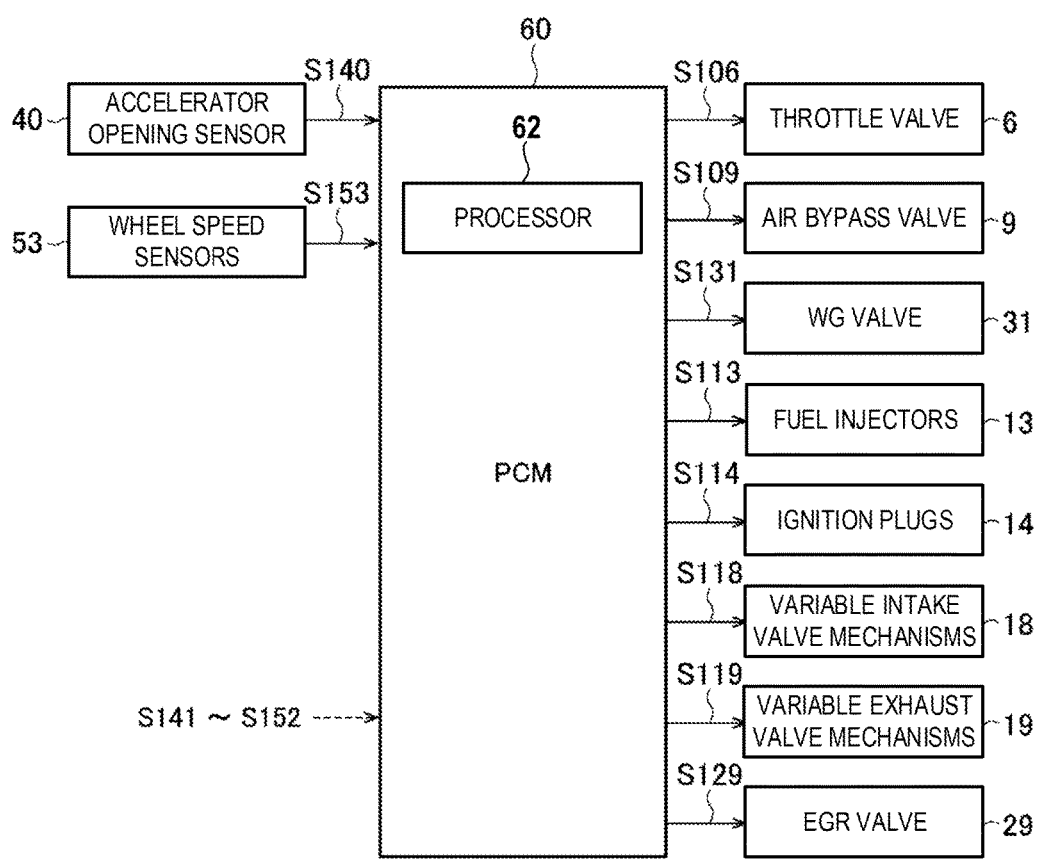
FIG. 2 is a block diagram illustrating an electric configuration of the misfire detecting system for the engine.

As illustrated in FIGS. 1 and 2, an engine system 100 mainly has an intake passage 1 through which intake air (air) externally introduced passes, an engine 10 (e.g., gasoline engine) for generating a drive force of a vehicle on which the engine 10 is mounted by combusting in cylinders a mixture gas of the intake air supplied from the intake passage 1 and fuel supplied from fuel injectors 13 (described later), an exhaust passage 25 through which an exhaust gas generated by the combustion inside the engine 10 is discharged, sensors 40 to 53 for detecting various states regarding the engine system 100, and a powertrain control module (PCM) 60 for controlling the entire engine system 100 as the misfire detecting system for the engine. Note that although only one cylinder is illustrated in FIG. 1, a plurality of (two or more) cylinders are actually provided to the engine 10.

In the intake passage 1, an air cleaner 3 for purifying the externally introduced intake air, a compressor 4a provided to a turbocharger 4 and for pressurizing the intake air passing therethrough, an intercooler 5 for cooling the intake air passing therethrough with outdoor air and a coolant, a throttle valve 6 for adjusting a flow rate of the intake air passing therethrough (intake air amount), and a surge tank 7 for temporarily storing intake air to be supplied to the engine 10 are disposed in this order from upstream side thereof.

Further in the intake passage 1, an air bypass passage 8 for recirculating a part of the intake air turbocharged by the compressor 4a back to an upstream side of the compressor 4a is provided. One end of the air bypass passage 8 is connected to the intake passage 1 at a position downstream of the compressor 4a and upstream of the throttle valve 6, and the other end of the air bypass passage 8 is connected to the intake passage 1 at a position downstream of the air cleaner 3 and upstream of the compressor 4a.

The air bypass passage 8 is provided with an air bypass valve 9 for controlling a flow rate of the intake air passing through the air bypass passage 8 by an open-close operation. The air bypass valve 9 is a so-called on-off valve switchable between a closed state where the air bypass passage 8 is fully closed, and an open state where the air bypass passage 8 is fully opened.

The engine 10 mainly has intake valves 12 for introducing the intake air supplied from the intake passage 1 into combustion chambers 11, respectively, the fuel injectors 13 for injecting the fuel into the combustion chambers 11, respectively, ignition plugs 14 for igniting the mixture gas of the intake air and the fuel supplied into the combustion chambers 11, respectively, pistons 15 for being reciprocated by the combustion of the mixture gas within the combustion chambers 11, respectively, a crankshaft 16 for rotating in relation to the reciprocations of the pistons 15, and exhaust valves 17 for discharging the exhaust gas generated by the combustion of the mixture gas within the combustion chambers 11 to the exhaust passage 25, respectively.

Moreover, the engine 10 is capable of varying operation timings (open and close timings) of the intake valves 12 by variable intake valve mechanisms 18, and varying operation timings (open and close timings) of the exhaust valves 17 by variable exhaust valve mechanisms 19, respectively. In this embodiment, those mechanisms are variable valve timing mechanisms. As the variable intake valve mechanisms 18 and the variable exhaust valve mechanisms 19, various known types may be applied. For example, the operation timings of the intake and exhaust valves 12 and 17 may be varied by using electromagnetic or hydraulic mechanisms.

In the exhaust passage 25, a turbine 4b provided to the turbocharger 4 and for rotating by letting exhaust gas pass therethrough so as to rotate the compressor 4a, and catalysts 35a and 35b (such as a $NO_x$ catalyst, three-way catalyst, or oxidation catalyst) having an exhaust gas purifying function are arranged in this order from the upstream side. Hereinafter, when referring to the catalysts 35a and 35b without differentiating therebetween, they are simply referred to as "the catalyst 35."

An exhaust gas recirculation (EGR) device 26 for recirculating a part of the exhaust gas back to the intake passage 1 as EGR gas is provided on the exhaust passage 25. The EGR device 26 includes an EGR passage 27 connected at one end to a position of the exhaust passage 25 upstream of the turbine 4b and connected at the other end to a position of the intake passage 1 downstream of the compressor 4a and further downstream of the throttle valve 6, an EGR cooler 28 for cooling the EGR gas, and an EGR valve 29 for controlling an amount (flow rate) of the EGR gas passing through the EGR passage 27. The EGR device 26 corresponds to a so-called high-pressure EGR device (HPL (High Pressure Loop) EGR device).

Moreover, the exhaust passage 25 is provided with a turbine bypass passage 30 for guiding the exhaust gas not to pass the turbine 4b of the turbocharger 4. This turbine bypass passage 30 is provided with a wastegate valve (hereinafter, referred to as "the WG valve") 31 for controlling a flow rate of the exhaust gas passing through the turbine bypass passage 30.

Furthermore, a part of the exhaust passage 25 between a connecting position with the upstream side of the EGR passage 27 and a connecting position with the upstream side of the turbine bypass passage 30 is branched into a first passage 25a and a second passage 25b. The first passage 25a has a larger diameter than the second passage 25b, and the first passage 25a is provided with a valve 25c. When the valve 25c is open, the exhaust gas basically flows to the first passage 25a, and when the valve 25c is closed, the exhaust gas flows only to the second passage 25b. Therefore, when the valve 25c is closed, the flow speed of the exhaust gas is higher than when the valve 25c is open. The valve 25c is closed within a low engine speed range so that the exhaust gas of which flow speed is increased is supplied to the turbine 4b of the turbocharger 4, thus, the turbocharging by the turbocharger 4 is performed also within the low engine speed range.

The engine system 100 is provided with the sensors 40 to 53 for detecting the various states regarding the engine system 100. That is, the accelerator opening sensor 40 detects an accelerator opening, i.e., an opening of an accelerator pedal (corresponding to a depression amount of the accelerator pedal by a vehicle driver). The airflow sensor 41 detects the intake air amount (corresponding to a flow rate of the intake air passing through the intake passage 1 between the air cleaner 3 and the compressor 4a). The temperature sensor 42 detects a temperature of the intake air passing through the intake passage 1 between the air cleaner 3 and the compressor 4a. The pressure sensor 43 detects a turbocharging pressure. The throttle opening sensor 44 detects a throttle opening, i.e., an opening of the throttle valve 6. The temperature sensor 45 detects a temperature of the intake air supplied to the engine 10 (intake air temperature). The crank angle sensor 46 detects a crank angle of the crankshaft 16. The intake cam angle sensor 47 detects a cam angle of an intake camshaft. The exhaust cam angle sensor 48 detects a cam angle of an exhaust camshaft. The temperature sensor 49 detects a temperature of the coolant of the engine 10 (coolant temperature). The WG opening sensor 50 detects an opening of the WG valve 31. The $O_2$ sensor 51 detects an oxygen concentration within the exhaust gas upstream of the catalyst 35a. The $O_2$ sensor 52 detects an oxygen concentration within the exhaust gas between the catalysts 35a and 35b. The wheel speed sensor(s) 53 detect speeds of drive wheels (corresponding to a vehicle speed). These various sensors 40 to 53 output detection signals S140 to S153 corresponding to detected parameters, to the PCM 60.

The PCM 60 controls components of the engine system 100 based on the detection signals S140 to S153 received from the various sensors 40 to 53 described above. For example, as illustrated in FIG. 2, the PCM 60 supplies a control signal S106 to the throttle valve 6 to control the open and close timings and opening of the throttle valve 6, the PCM 60 supplies a control signal S109 to the air bypass valve 9 to cause the air bypass valve 9 to open/close, the PCM 60 supplies a control signal S131 to the WG valve 31 to control the opening of the WG valve 31, the PCM 60 supplies a control signal S113 to the fuel injectors 13 to control the fuel injection amount and the fuel injection timing, the PCM 60 supplies a control signal S114 to the ignition plugs 14 to control the ignition timing, the PCM 60 supplies control signals S118 and S119 to the variable intake valve mechanisms 18 and the variable exhaust valve mechanisms 19 to control the operation timings of the intake valves 12 and the exhaust valves 17, and the PCM 60 supplies a control signal S129 to the EGR valve 29 to control the opening of the EGR valve 29.

Especially in this embodiment, the PCM 60 performs a misfire determination in which a misfire of the engine 10 is detected based on the crank angle detected by the crank angle sensor 46. Further, the PCM 60 performs a slip determination to detect wheel slip based on the wheel speeds detected by the wheel speed sensors 53. Additionally, when the misfire of the engine 10 is determined to have occurred, the PCM 60 turns on an alarm lamp to inform a driver of an abnormality relating to the misfire of the engine 10, i.e., turns on an MIL (Malfunction Indication Lamp) for informing the driver of the abnormality. Thus, the PCM 60 may be referred to as "the misfire detecting system for the engine."

Note that the PCM 60 comprises a computer including a processor (e.g., CPU) 62, internal memories such as ROM(s) and RAM(s) for storing various programs which are interpreted and executed by the processor 62 (the programs include a basic control program (e.g., OS) and an application program activated on the OS and for achieving a particular function), and various data.

<Outline of Misfire Determination in this Embodiment>

First, an outline of the misfire determination in this embodiment of the present invention is described. In this embodiment, in the misfire determination of the engine 10 based on the crank angle detected by the crank angle sensor 46, the PCM 60 determines the wheel slip based on change rates of the wheel speeds before performing the misfire determination, and if the wheel slip is determined to have occurred, the PCM 60 limits (i.e., prohibits) the misfire determination. By this, a situation is prevented in which when torsion occurs in the driveshaft by the wheel slip and the crank angle greatly fluctuates, the fluctuation of the crank angle is considered to be caused by the misfire of the engine 10 and the misfire of the engine 10 is falsely determined to have occurred. Especially in this embodiment, the PCM 60 changes, according to an engine load, a determination reference value for determining the change rates of the wheel speeds to accurately determine the wheel slip and suitably determine whether to perform the misfire determination (hereinafter, referred to as "the slip determination reference value").

Moreover in this embodiment, the PCM 60 changes a determination reference value for determining the misfire of the engine 10 based on the crank angle (hereinafter, referred to as "the misfire determination reference value"), based on a density of the intake air introduced into the engine 10. For example, the PCM 60 obtains the fluctuation (absolute value) of a crank angular acceleration based on the detection signal of the crank angle sensor 46, and determines that the misfire has occurred when the fluctuation of the crank angular acceleration is equal to or greater than the misfire determination reference value. When the intake air density is high, the PCM 60 sets the misfire determination reference value to be higher than when the intake air density is low, so that the frequency of misfire determination is reduced. In this manner, when a variation of an intake air introducing amount (charging amount) into each cylinder increases due to the high intake density and the fluctuation of the crank angle increases, this crank angle fluctuation is prevented from being considered to have been caused by the misfire of the engine 10, which would lead to the false determination of the misfire of the engine 10. Especially in this embodiment, the PCM 60 determines the intake air density based on a temperature of the intake air introduced into the engine 10 or an outdoor air temperature. Here, if the intake air temperature or the outdoor air temperature is low, the PCM 60 considers that the intake air density is higher than when the temperature is high, and increases the misfire determination reference value.

<Slip Determination>

Figure 3:
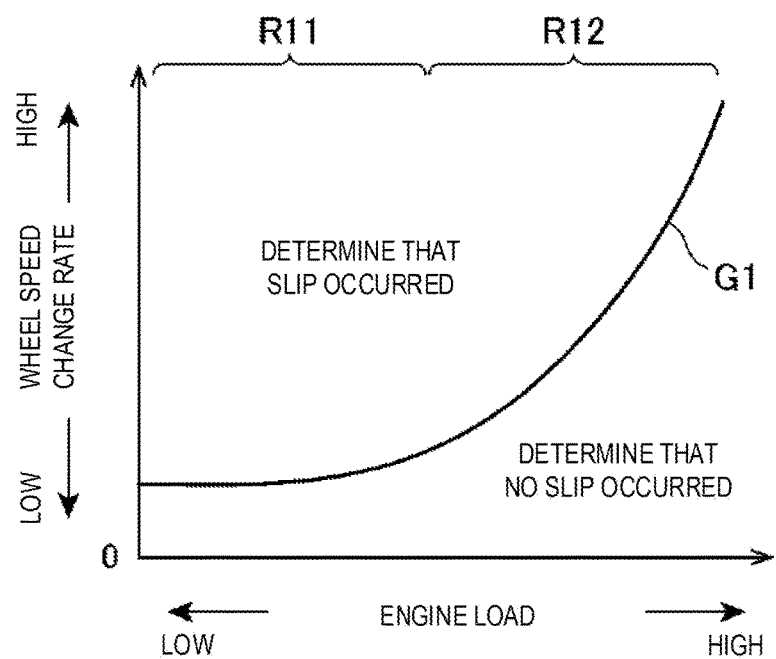
FIG. 3 is a chart illustrating a slip determination.

Next, the slip determination of this embodiment of the present invention is described in detail with reference to FIG. 3 in which the horizontal axis indicates the engine load and the vertical axis indicates a wheel speed change rate. In FIG. 3, the solid line G1 indicates the slip determination reference value for examining the wheel speed change rate in the slip determination. The PCM 60 determines that the wheel slip has occurred if the wheel speed change rate is equal to or greater than the slip determination reference value, and determines that the wheel slip has not occurred if the wheel speed change rate is lower than the slip determination reference value. Note that the wheel speed change rate is a change rate of the wheel speed in a given period of time (typically, a change rate of the wheel speed per unit time).

As illustrated in FIG. 3, the slip determination reference value is basically higher when the engine load is high than when it is low. For example, the slip determination reference value increases as the engine load increases. Particularly a change rate of the slip determination reference value with respect to a change of the engine load increases as the engine load increases (i.e., it increases in a quadratic curve shape). For example, such a slip determination reference value is obtained by measuring through experiments the wheel speed change rates when the slip has occurred and when the slip has not occurred, in terms of various engine loads.

Note that in FIG. 3, a low engine load range (R11) where a comparatively low slip determination reference value is set, corresponds to a no-turbocharging range where the turbocharging by the turbocharger 4 is not performed, and a high engine load range (R12) where a slip determination reference value relatively higher than within the no-turbocharging range is set, corresponds to a turbocharging range where the turbocharging by the turbocharger 4 is performed.

The reason for setting the slip determination reference value as above is as follows. Normally when the engine load (combustion torque) increases, within the high engine load range, such as the turbocharging range R12, the wheel speed tends to change more. For example, within the high engine load range, the wheel speed tends to change more than when the wheel slip occurs within the low engine load range, such as the no-turbocharging range R11 (needless to say that the wheel speed changes even more when the wheel slip occurs within the high engine load range). Therefore in this embodiment, the slip determination reference value is increased as the engine load increases (in other words, the slip determination reference value is reduced as the engine load decreases) so as to prevent the false determination of the slip within the high engine load range while securing the accuracy of the slip determination within the low engine load range. Thus, with the configuration of limiting the misfire determination at the time of slip occurrence so as to prevent the false determination of the misfire, by preventing the false slip determination through using a suitable slip determination reference value, the misfire determination is prevented from being unnecessarily limited even though the slip has not occurred, and a suitable frequency of performing the misfire determination is secured.

<Misfire Determination According to Outdoor Air Temperature>

Figure 4:
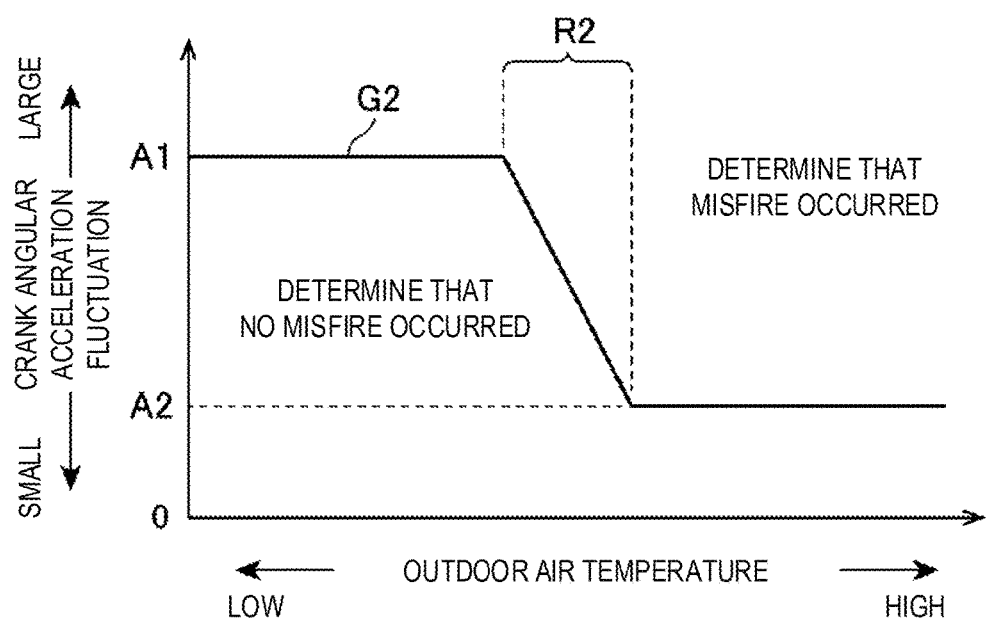
FIG. 4 is a chart illustrating a misfire determination.

Next, the misfire determination taking into consideration the outdoor air temperature relating to the intake air density in this embodiment of the present invention is described with reference to FIG. 4 in which the horizontal axis indicates the outdoor air temperature and the vertical axis indicates the fluctuation (absolute value) of the crank angular acceleration. In FIG. 4, the solid line G2 indicates the misfire determination reference value for determining the fluctuation of the crank angular acceleration in the misfire determination. The PCM 60 determines that the misfire of the engine 10 has occurred if the fluctuation of the crank angular acceleration is equal to or greater than the misfire determination reference value, and determines that the misfire of the engine 10 has not occurred if the fluctuation of the crank angular acceleration is lower than the misfire determination reference value. Note that the fluctuation of the crank angular acceleration is a change rate of the crank angular acceleration in a given period of time.

As illustrated in FIG. 4, the misfire determination reference value is higher when the outdoor air temperature is low (e.g., below 0° C.) than when it is high (e.g., 20° C. or above). For example, within a range where the outdoor air temperature falls lower than a given range R2 (e.g., between 0° C. and 20° C.), the misfire determination reference value is set to a value indicated by the reference character A1, and within a range where the outdoor air temperature exceeds the given range R2, the misfire determination reference value is set to a value indicated by the reference character A2, which is lower than the misfire determination reference value A1 described above. When the outdoor air temperature is within the given range R2, the misfire determination reference value is set to a value between the misfire determination values A1 and A2 described above, according to the outdoor air temperature. That is, when the outdoor air temperature is within the given range R2, the misfire determination reference value changes between A1 and A2 according to the outdoor air temperature. For example, such a misfire determination reference value is obtained by measuring through experiments, simulations etc. the crank angular acceleration fluctuations when the misfire has occurred and when the misfire has not occurred, in terms of various outdoor air temperatures.

Note that the misfire determination reference value is basically set based on the engine speed and load, and FIG. 4 illustrates an example of the misfire determination reference value according to the outdoor air temperature, applied at a certain engine speed and load.

The reason for setting the misfire determination reference value as above is as follows. The intake air introducing amount (charging amount) into each cylinder slightly varies depending on the shape of an intake manifold, the smoothness of the intake air flow into the cylinder (or, roughness of the intake air flow), etc. Since the intake air density becomes high when the outdoor air temperature becomes low, such a variation of the intake air introducing amount among the cylinders becomes large. Therefore the combustion variation among the cylinders becomes large and the crank angle tends to fluctuate greatly. Thus in this embodiment, when the outdoor air temperature is low, the misfire determination reference value is set higher than when the outdoor air temperature is high, so as to prevent that such a fluctuation of the crank angle which occurs when the intake air density is high is falsely determined as the misfire of the engine 10. By this, the false determination of the misfire when the intake air density is high (i.e., the outdoor air temperature is low) is prevented while securing the accuracy of the misfire determination when the intake air density is low (i.e., the outdoor air temperature is high).

Note that in the above description, the example in which the misfire determination reference value is set based on the outdoor air temperature is given; however, the misfire determination reference value may be set based on the intake air temperature instead of the outdoor air temperature. Also in this case, similar to FIG. 4, the misfire determination reference value is defined according to the intake air temperature. Since the engine 10 of this embodiment receives the intake air turbocharged by the turbocharger 4, the misfire determination reference value may be set using the temperature of the intake air after being turbocharged by the turbocharger 4 and passing through the intercooler 5 (the temperature detected by the temperature sensor 45).

<Misfire Determination Processing>

Figure 5:
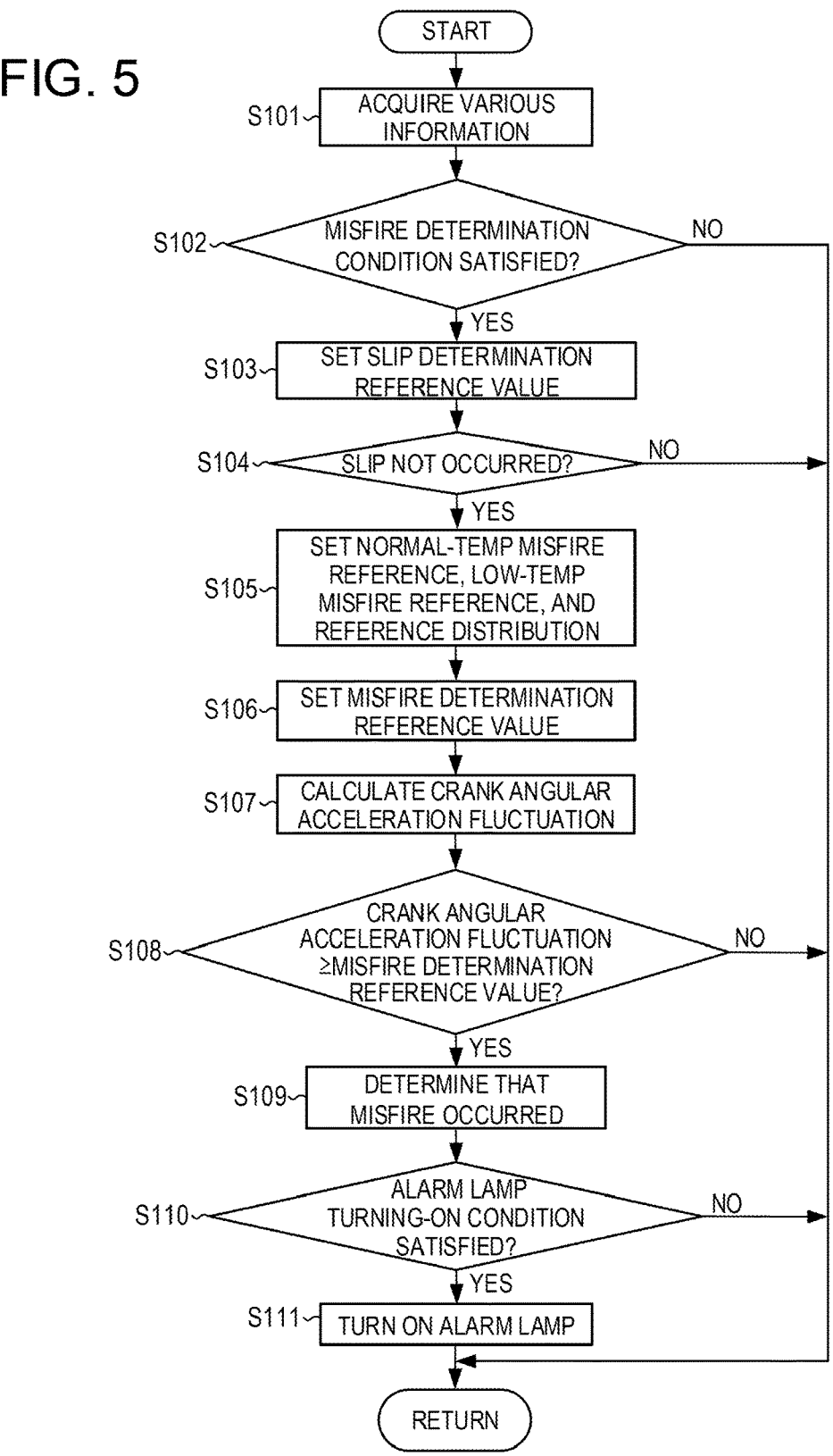
FIG. 5 is a flowchart of misfire determination processing.

Next, detailed processing of the misfire determination of this embodiment of the present invention is described with reference to FIG. 5, which is a flowchart of the misfire determination processing. This misfire determination processing is repeatedly executed at a given cycle by the PCM 60, specifically, the processor 62.

First at S101, the PCM 60 acquires various information of the vehicle. Particularly, the PCM 60 acquires the intake air temperature detected by the temperature sensor 45, the crank angle detected by the crank angle sensor 46, the wheel speed detected by the wheel speed sensor 53, etc.

Then at S102, the PCM 60 determines whether a misfire determination condition is satisfied. For example, the PCM 60 determines the misfire determination condition as satisfied (S102: YES) when a gear change is not performed, a fuel-cut is not performed, the engine coolant temperature is equal to or greater than a given temperature, and further the engine speed is equal to or greater than a given speed, and proceeds to S103. On the other hand, when the gear change is performed, the fuel-cut is performed, the engine coolant temperature is less than the given temperature, or the engine speed is lower than the given speed, the PCM 60 determines the misfire determination condition as not satisfied (S102: NO). In this case, the PCM 60 terminates the flow of the misfire determination processing without performing the misfire determination.

At S103, the PCM 60 sets the slip determination reference value based on the engine load. For example, the PCM 60 sets the slip determination reference value corresponding to a current engine load based on a map of the slip determination reference value illustrated in FIG. 3.

Next at S104, the PCM 60 obtains the wheel speed change rate based on the wheel speed detected by the wheel speed sensor 53, and determines whether the wheel slip has occurred by comparing the wheel speed change rate with the slip determination reference value set at S103. The PCM 60 determines that the slip has not occurred if the wheel speed change rate is lower than the slip determination reference value (S104: YES) and proceeds to S105. At S105 and thereafter, the PCM 60 executes processing to actually perform the misfire determination. On the other hand, the PCM 60 determines that the slip has occurred if the wheel speed change rate is equal to or greater than the slip determination reference value (S104: NO). In this case, the PCM 60 terminates the flow of the misfire determination processing without performing the misfire determination.

At S105, the PCM 60 sets a normal-temperature misfire reference, a low-temperature misfire reference, and a reference distribution, which are used for setting the misfire determination reference value. These normal- and low-temperature misfire references and the reference distribution are used for setting the misfire determination reference value corresponding to the engine speed, the engine load, and the outdoor air temperature. For example, the normal-temperature misfire reference corresponds to the misfire determination reference value to be applied according to the engine speed and load when the outdoor air temperature is normal (e.g., 25° C.), and the low-temperature misfire reference corresponds to the misfire determination reference value to be applied according to the engine speed and load when the outdoor air temperature is low (e.g., below 0° C.). Further, the reference distribution corresponds to a distribution ratio between the normal-temperature misfire reference and the low-temperature misfire reference according to the outdoor air temperature in determining the misfire determination reference value to be applied finally. By adding the normal-temperature misfire reference and the low-temperature misfire reference according to the reference distribution, the misfire determination reference value to be applied finally is set.

Figure 6A:
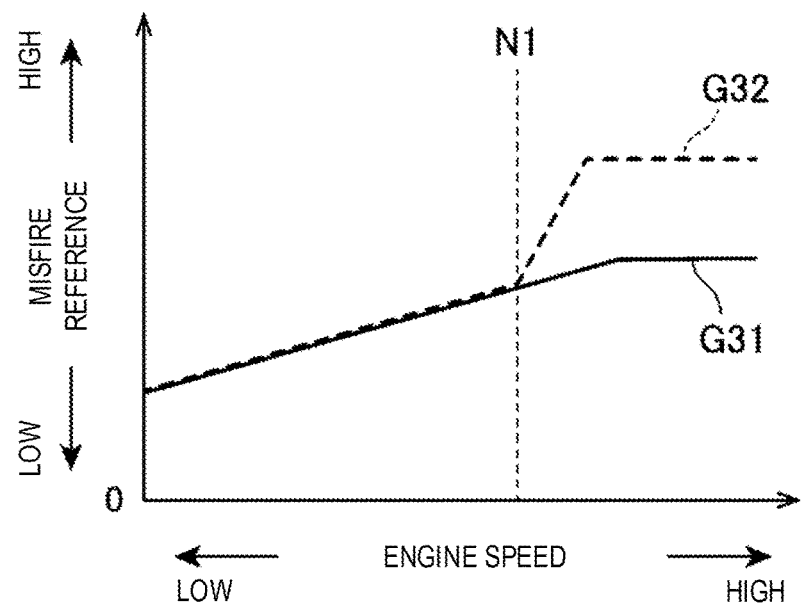
FIGS. 6A and 6B show charts, each illustrating a normal-temperature misfire reference and a low-temperature misfire reference.
Figure 6B:
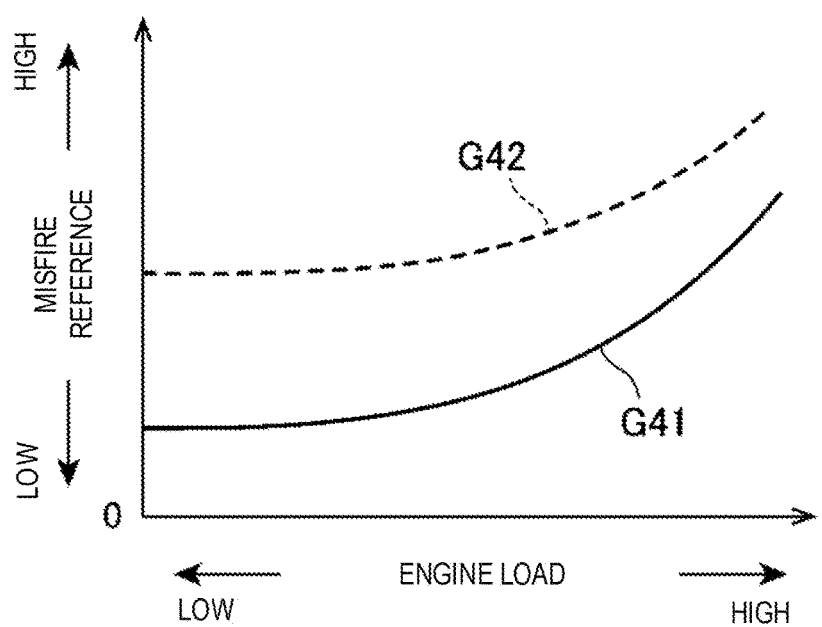
Figure 7:
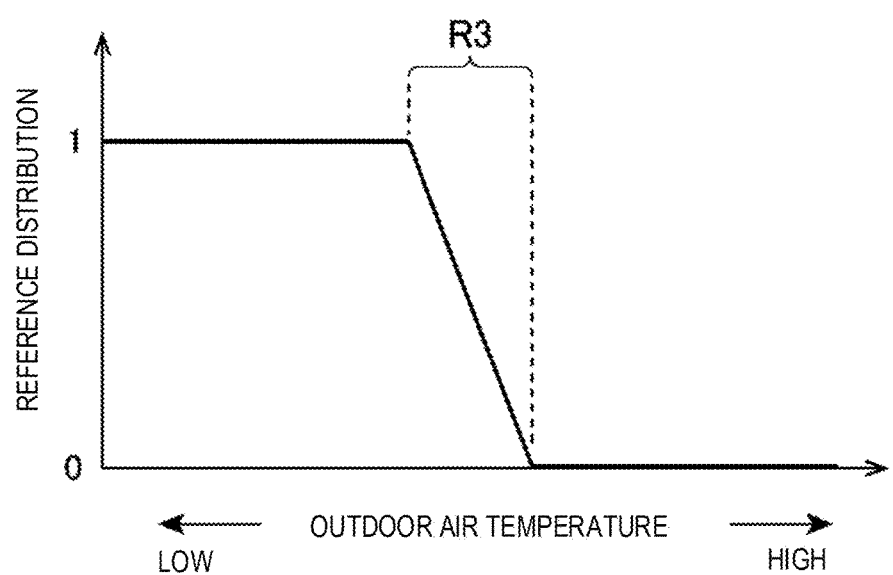
FIG. 7 is a chart illustrating a reference distribution.

Here, a method of setting the normal-temperature misfire reference, the low-temperature misfire reference, and the reference distribution is described in detail with reference to FIGS. 6A, 6B and 7. FIGS. 6A and 6B show charts, each illustrating the normal-temperature misfire reference and the low-temperature misfire reference. FIG. 7 is a chart illustrating the reference distribution.

FIG. 6A is a chart illustrating a relationship between the engine speed (horizontal axis) and the misfire reference (vertical axis) at a fixed engine load. In FIG. 6A, the solid line G31 indicates the normal-temperature misfire reference, and the dashed line G32 indicates the low-temperature misfire reference. As illustrated in FIG. 6A, basically, both of the normal- and low-temperature misfire references become higher as the engine speed increases at the fixed engine load.

Particularly in this embodiment, within a range above an engine speed N1, the normal- and low-temperature misfire references are set to be different. For example, when exceeding the engine speed N1, an increase amount of the misfire reference corresponding to an increase of the engine speed is set to be larger for the low-temperature misfire reference than the normal-temperature misfire reference. This is because the crank angle fluctuation caused by the variation of the intake air introducing amount among the cylinders becomes large within the high engine speed range under a low outdoor air temperature (i.e., the crank angle fluctuation becomes small within the low engine speed range even under a low outdoor air temperature). Therefore in this embodiment, in order to prevent that a comparatively large crank angle fluctuation which occurs within the high engine speed range under such a low outdoor air temperature is falsely determined as the misfire, the low-temperature misfire reference is set larger than the normal-temperature misfire reference within the range above the engine speed N1.

FIG. 6B is a chart illustrating a relationship between the engine load (horizontal axis) and the misfire reference (vertical axis) at a fixed engine speed higher than the engine speed N1 described above. In FIG. 6B, the solid line G41 indicates the normal-temperature misfire reference, and the dashed line G42 indicates the low-temperature misfire reference. As illustrated in FIG. 6B, basically, both of the normal- and low-temperature misfire references become higher as the engine load increases at the fixed engine speed. Especially in this embodiment, within the high engine speed range above the engine speed N1, over substantially the entire engine load range, the low-temperature misfire reference is set larger than the normal-temperature misfire reference. Since the crank angle fluctuation becomes large within the high engine speed range under the low outdoor air temperature as described above, the low-temperature misfire reference is set larger to reliably prevent that this crank angle fluctuation is falsely determined as the misfire.

Note that within a range below the engine speed N1 which is not illustrated in FIG. 6B, the relationship between the engine load and the misfire reference is the same with the normal-temperature misfire reference and the low-temperature misfire reference (i.e., the same value is set according to the engine load). Also within the range below the engine speed N1, both of the normal- and low-temperature misfire references are basically set higher as the engine load increases.

Moreover, the normal-temperature misfire references illustrated in FIGS. 6A and 6B are obtained by measuring through experiments, simulations etc. the crank angular acceleration fluctuations when the misfire has occurred and when the misfire has not occurred at the normal temperature (e.g., 25° C.), in terms of various engine speeds and loads. Similarly, the low-temperature misfire references are obtained by measuring through experiments, simulations etc. the crank angular acceleration fluctuations when the misfire has occurred and when the misfire has not occurred at the low temperature (e.g., below 0° C.), in terms of various engine speeds and loads.

FIG. 7 is a chart illustrating a relationship between the outdoor air temperature (horizontal axis) and the reference distribution (vertical axis). The reference distribution indicates a ratio of the low-temperature misfire reference with respect to the normal-temperature misfire reference. For example, when the reference distribution is "1," the distribution of the low-temperature misfire reference is "1" and the distribution of the normal-temperature misfire reference is "0." In this case, the misfire determination reference value to be applied finally becomes the low-temperature misfire reference. On the other hand, when the reference distribution is "0," the distribution of the low-temperature misfire reference is "0" and the distribution of the normal-temperature misfire reference is "1." In this case, the misfire determination reference value to be applied finally becomes the normal-temperature misfire reference.

As illustrated in FIG. 7, the reference distribution is larger when the outdoor air temperature is low (e.g., below 0° C.) than when it is high (e.g., 20° C. or above). For example, the reference distribution is set to "1" when the outdoor air temperature is lower than a given range R3 (e.g., between 0° C. and 20° C.), the reference distribution is set to "0" when the outdoor air temperature is above the given range R3, and the reference distribution is set to a value between "0" and "1" according to the outdoor air temperature when the outdoor air temperature is within the given range R3. In other words, when the outdoor air temperature is within the given range R3, the reference distribution changes between "0" and "1" according to the outdoor air temperature.

Note that the outdoor air temperature range for setting such a reference distribution corresponds to the outdoor air temperature range for setting the misfire determination reference value illustrated in FIG. 4. FIG. 4 illustrates one example of the relationship between the outdoor air temperature and the misfire determination reference value, which is obtained based on the normal- and low-temperature misfire references set according to a given engine speed exceeding the engine speed N1 and a given engine load.

Returning to FIG. 5, the explanation of S105 is resumed. At S105, the PCM 60 determines the normal- and low-temperature misfire references corresponding to a current engine speed and load (see FIG. 6) and determines the reference distribution corresponding to a current outdoor air temperature (see FIG. 7). Here, the PCM 60 determines the reference distribution by using an outdoor air temperature estimated based on the intake air temperature detected by the temperature sensor 45 or by providing an outdoor air temperature sensor to the vehicle and using an outdoor air temperature detected by this outdoor air temperature sensor. Note that the reference distribution may be set based on the intake air temperature instead of the outdoor air temperature. In this case, the reference distribution may be determined based on the intake air temperature detected by the temperature sensor 45.

Next at S106, the PCM 60 sets the misfire determination reference value based on the normal- and low-temperature misfire references and the reference distribution, which are set at S105. For example, the PCM 60 obtains the misfire determination reference value by adding the normal- and low-temperature misfire references according to the reference distribution.

Next at S107, the PCM 60 calculates the crank angular acceleration fluctuation (absolute value) based on the crank angle detected by the crank angle sensor 46. For example, the PCM 60 repeatedly obtains the crank angular acceleration based on the rotational cycle measured by the crank angle sensor 46 to sample them, filters (e.g., high-pass filters) the sampled crank angular accelerations, and then obtains the change rate of the crank angular acceleration in the given time period as the crank angular acceleration fluctuation.

Next at S108, the PCM 60 determines whether the crank angular acceleration fluctuation obtained at S107 is equal to or greater than the misfire determination reference value set at S106. The determination corresponds to a determination of whether fluctuation of the crank angle corresponding to a great deceleration caused by the misfire has occurred.

If the crank angular acceleration fluctuation is equal to or greater than the misfire determination reference value (S108: YES), the PCM 60 proceeds to S109 where the misfire of the engine 10 is determined to have occurred. In this case, the PCM 60 also identifies the cylinder in which the misfire has occurred among the plurality of cylinders. On the other hand, if the crank angular acceleration fluctuation is lower than the misfire determination reference value (S108: NO), the PCM 60 terminates the flow of the misfire determination processing. In this case, the PCM 60 determines that the misfire of the engine 10 has not occurred.

After S109, at S110, the PCM 60 determines whether a condition to turn on an alarm lamp for informing of an abnormality relating to the misfire of the engine 10 (alarm lamp turning-on condition) is satisfied. The PCM 60 determines whether the alarm lamp turning-on condition is satisfied, respectively for an alarm lamp which turns on for protection of the catalyst 35 (hereinafter referred to as "the catalyst alarm lamp") and an alarm lamp which turns on to inform of emission degradation (hereinafter referred to as "the emission alarm lamp"). The alarm lamp turning-on condition for the catalyst alarm lamp is satisfied when the number of times the misfire has occurred by the time that the speed (combustion frequency) of the engine 10 reaches a first value is equal to or greater than a second value. This second value may be changed according to the engine speed and the intake air amount. On the other hand, the alarm lamp turning-on condition for the emission alarm lamp is satisfied when the number of times the misfire has occurred by the time that the speed (combustion frequency) of the engine 10 reaches a third vale (>first value) is equal to or greater than a fourth value.

If the alarm lamp turning-on condition for one of the catalyst alarm lamp and the emission alarm lamp is determined as satisfied (S110: YES), the PCM 60 proceeds to S111 to turn on the one of the catalyst alarm lamp and the emission alarm lamp. On the other hand, if the alarm lamp turning-on condition for neither of the catalyst alarm lamp and the emission alarm lamp is determined as satisfied (S110: NO), the PCM 60 terminates the flow of the misfire determination processing. In this case, the PCM 60 does not turn on the catalyst alarm lamp and the emission alarm lamp.

<Operations and Effects>

Next, the operations and effects of the misfire detecting system for the engine according to this embodiment of the present invention are described.

According to this embodiment, the misfire determination reference value is set by taking into consideration the intake air density according to the intake air temperature or the outdoor air temperature, and the misfire determination is performed by using this misfire determination reference value. Therefore, it is possible to prevent the crank angle fluctuation, which is caused by the variation of the intake air introducing amount among the cylinders becoming large due to the high intake air density, from being falsely determined to have been caused by the misfire of the engine 10. Thus, according to this embodiment, it is possible to suitably prevent the false determination of the misfire when the intake air density is high while securing the accuracy of the misfire determination when the intake air density is low.

Further according to this embodiment, within the high engine speed range above the engine speed N1, the low-temperature misfire reference is increased and the misfire determination reference value to be applied finally is changed upward. Thus, the misfire determination reference value is set suitably by taking into consideration the characteristic that the crank angle fluctuation becomes large within the high engine speed range under a low temperature. Therefore, it is possible to effectively prevent the false determination of the misfire.

Further according to this embodiment, as illustrated in FIG. 4, within the range where the outdoor air temperature is lower than the given range R2, the misfire determination reference value A1 is applied, and within the range where the outdoor air temperature is above the given range R2, the misfire determination reference value A2 which is lower than the value A1 is applied. Therefore, it is possible to prevent the false determination of the misfire when the outdoor air temperature is low (i.e., the intake air density is high) while securing the accuracy of the misfire determination when the outdoor air temperature is high (i.e., the intake air density is low). Moreover, when the outdoor air temperature is within the given range R2, a misfire determination reference value between A1 and A2 is applied according to the outdoor air temperature. Thus, within this temperature range, the misfire determination reference value is suitably changed according to the outdoor air temperature by taking into consideration the responsiveness of the temperature sensor 45.

Further according to this embodiment, the misfire determination is performed based on the crank angular acceleration fluctuation. Therefore, compared to a case of performing the misfire determination based on a fluctuation of a crank angular speed or a magnitude of the crank angular acceleration, fluctuation of the crank angle caused by the misfire is suitably captured, which improves the accuracy of the misfire determination.

Moreover according to this embodiment, since the alarm lamp is turned on when the misfire of the engine 10 is determined to have occurred, it is possible to suitably inform the driver of the abnormality relating to the misfire.

<Modifications>

In the embodiment described above, the misfire determination is performed based on the crank angular acceleration fluctuation; however, in a different example, the misfire determination may be performed based on one of a fluctuation of the crank angle itself, a fluctuation of a crank angular speed, and the magnitude of the crank angular acceleration.

In the embodiment described above, the example in which the present invention is applied to the gasoline engine is described; however, the present invention may be applied to a diesel engine. Further in the embodiment described above, the example in which the present invention is applied to the engine with the turbocharger is described; however, the application of the present invention is not limited to this.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof, are therefore intended to be embraced by the claims.

LIST OF REFERENCE CHARACTERS

1 Intake Passage
4 Turbocharger
6 Throttle Valve
10 Engine
11 Combustion Chamber
12 Intake Valve
13 Fuel Injector
14 Ignition Plug
15 Piston
17 Exhaust Valve
25 Exhaust Passage
26 EGR Device
35*a*, 35*b* Catalyst
60 PCM
100 Engine System

What is claimed is:

1. A misfire detecting system for an engine of a vehicle that detects a misfire of the engine, the misfire detecting system comprising:
   a crank angle sensor configured to detect a crank angle of a crank shaft of the engine;
   an intake air temperature sensor configured to detect a temperature of an intake air; and
   a processor operatively coupled to the crank angle sensor and the intake air temperature sensor and configured to:
   calculate a crank angular acceleration fluctuation based on the crank angle detected by the crank angle sensor;
   determine whether a misfire has occurred by examining whether the crank angular acceleration fluctuation is equal to or greater than a determination reference value, wherein
   the determination reference value is set to a first value when the detected temperature of the intake air is a first temperature;
   the first value is higher than a second value that is set when the detected temperature is a second temperature, which is higher than the first temperature so as to prevent a false determination of the misfire; and
   the processor outputs an indication to alert an abnormality relating to the misfire of the engine, when the misfire is determined.

2. The misfire detecting system of claim 1, wherein the processor changes the determination reference value based on an engine speed and an engine load, and a change amount of the determination reference value in accordance with the temperature of the intake air is larger when the engine speed is high, compared to when the engine speed is low.

3. The misfire detecting system of claim 1, wherein the processor adjusts the determination reference value between the first and second values according to the temperature of the intake air when the temperature of the intake air is within a given range between the first temperature and the second temperature.

4. The misfire detecting system of claim 1, wherein the engine is provided with a turbocharger.

5. The misfire detecting system of claim 1, wherein the determination reference value is set by the detected temperature so as to take into consideration an intake air density.

6. The misfire detecting system of claim 1, wherein outputting the indication is accomplished by turning on an alarm lamp.

7. A misfire detecting system for an engine of a vehicle that detects a misfire of the engine, the misfire detecting system comprising: a crank angle sensor configured to detect a crank angle of a crank shaft of the engine; and a processor operatively coupled to the crank angle sensor and configured to:
  obtain a temperature of an intake air;
  calculate a crank angular acceleration fluctuation based on the crank angle detected by the crank angle sensor;
  determine whether a misfire has occurred by examining whether the crank angular acceleration fluctuation is equal to or greater than a determination reference value, wherein
  the determination reference value is set to a first value when the obtained temperature of the intake air is a first temperature;
  the first value is higher than a second value that is set when the obtained temperature is a second temperature, which is higher than the first temperature so as to prevent a false determination of the misfire; and
  the processor outputs an indication to alert an abnormality relating to the misfire of the engine, when the misfire is determined.

8. The misfire detecting system of claim 7, wherein the temperature of the intake air is obtained from an intake air temperature sensor.

9. The misfire detecting system of claim 7, wherein outputting the indication is accomplished by turning on an alarm lamp.

* * * * *